United States Patent
Marchitto et al.

(10) Patent No.: US 6,532,387 B1
(45) Date of Patent: Mar. 11, 2003

(54) CATHETER FOR DELIVERING ELECTROMAGNETIC ENERGY FOR ENHANCED PERMEATION OF SUBSTANCES

(76) Inventors: Kevin S. Marchitto, 127 Bellbird Road, Mt. Eliza 3930 VIC (AU); Stephen T. Flock, 17 Gillards Road, Mt. Eliza 3930 (AU)

( * ) Notice: Subject to any disclaimer, the term of this patent is extended or adjusted under 35 U.S.C. 154(b) by 0 days.

(21) Appl. No.: 09/534,688

(22) Filed: Mar. 24, 2000

Related U.S. Application Data

(60) Provisional application No. 60/126,294, filed on Mar. 26, 1999, now abandoned.

(51) Int. Cl.[7] .................................................. A61N 1/30
(52) U.S. Cl. ........................... 604/21; 604/506; 606/33; 606/15; 607/154
(58) Field of Search ................... 604/500, 21, 506–509, 604/96.01, 101.01, 101.03, 101.05; 606/33, 15, 16; 607/154

(56) References Cited

U.S. PATENT DOCUMENTS

| | | | |
|---|---|---|---|
| 4,175,545 A | | 11/1979 | Termanini |
| 4,770,653 A | * | 9/1988 | Shturman ........................ 606/7 |
| 5,041,121 A | * | 8/1991 | Wondrazek et al. ........... 606/15 |
| 5,125,417 A | * | 6/1992 | Nebenzahl ................... 330/1 R |
| 5,152,277 A | * | 10/1992 | Honda et al. ........... 604/101.03 |
| 5,152,768 A | * | 10/1992 | Bhatta ............................ 601/4 |
| 5,246,437 A | * | 9/1993 | Abela ........................... 604/20 |
| 5,386,837 A | * | 2/1995 | Sterzer ........................ 128/898 |
| 5,419,312 A | * | 5/1995 | Arenberg et al. ............ 600/108 |
| 5,643,252 A | * | 7/1997 | Waner et al. .................. 604/21 |
| 5,817,144 A | | 10/1998 | Gregory |
| 5,823,993 A | * | 10/1998 | Lemelson .................... 128/898 |
| 5,836,940 A | * | 11/1998 | Gregory ....................... 604/20 |
| 5,999,847 A | * | 12/1999 | Elstrom ........................ 604/20 |
| 6,033,371 A | * | 3/2000 | Torre et al. ..................... 601/2 |
| 6,076,005 A | * | 6/2000 | Sontag et al. ................. 378/62 |
| 6,077,257 A | * | 6/2000 | Edwards et al. ............. 604/506 |
| 6,165,440 A | * | 12/2000 | Esenaliev .................... 264/473 |
| 6,187,023 B1 | * | 2/2001 | Bonutti ....................... 606/190 |
| 6,224,566 B1 | | 5/2001 | Loeb |
| 6,251,100 B1 | * | 6/2001 | Flock et al. ................... 604/20 |
| 6,290,712 B1 | * | 9/2001 | Nordquist et al. .......... 128/898 |
| 6,317,630 B1 | * | 11/2001 | Gross et al. ................... 604/20 |
| 6,366,818 B1 | * | 4/2002 | Bolmsjo ....................... 606/33 |

OTHER PUBLICATIONS

Gregory et al, "Liquid Core Light Guide for Laser Angioplasty", IEEE Journal of Quantum Electronics, vol. 26, No. 12, Dec. 1990, p. 2289–2296.*

* cited by examiner

Primary Examiner—Michael J. Hayes
Assistant Examiner—Jeremy Thissell
(74) Attorney, Agent, or Firm—Benjamin Aaron Adler

(57) ABSTRACT

The present invention provides a catheter device/method for enhancing local administration of pharmaceutical compounds. Such device/method is used for various situations which require high concentrations of drugs that are delivered locally.

4 Claims, 4 Drawing Sheets

CATHETER FOR DELIVERING ELECTROMAGNETIC ENERGY FOR ENHANCED PERMEATION OF SUBSTANCES

CROSS-REFERENCE TO RELATED APPLICATION

This non-provisional patent application claims benefit of provisional patent application U.S. Ser. No. 60/126,294, filed Mar. 26, 1999, now abandoned.

BACKGROUND OF THE INVENTION

1. Field of the Invention

The present invention relates generally to the fields of medical physics and drug delivery. More specifically, the present invention relates to catheter devices for delivering electromagnetic energy to enhance permeation of substances.

2. Description of the Related Art

The human body is composed of a variety of passageways including blood vessels, intestines, urinary passages, etc. These passageways may, at times, provide unique access to surrounding tissues and organs. For example, the prostate gland is located anatomically in a position that is juxtaposed to the colon and bladder. Thus, by traversing the membranes of the colon or bladder, direct local access to the prostate and surrounding tissue is possible. In this way, these body passageways become a route for local delivery of substances.

At other times these passageways may be the site of abnormal growths which cause obstructions and other problems. As a result, tissues and organs beyond these obstructions may be starved for nutrients. Alternatively, the obstructions may prevent drainage of waste materials. Some growths such as tumors may ultimately starve the surrounding tissues or produce toxic substances themselves. Thus, the effects of these obstructions may ultimately lead to toxicity and even death.

Cells and materials which commonly form obstructions are capable of being dissolved or removed by various chemical agents. Nevertheless, achieving effective concentrations of these agents systemically is very difficult as they are often toxic in large doses or have serious side effects. For example, the clot dissolving agent Tissue Plasminogen Activator (TPA) is effective at dissolving the kind of blood clots found in coronary restenosis or in deep vein thrombosis (DVT). However, when administered systemically in doses great enough to affect regions of the heart or distal venous regions of the leg, the drugs cause side effects which can lead to hemorrhage or other forms of internal bleeding. Thus, it is desirable to deliver high concentrations of TPA to local regions of the heart or venous portions of the leg without affecting distal and surrounding tissues and organs.

The prior art is deficient in the lack of effective means of delivering non-ionizing electromagnetic energy for enhancing drug delivery. The present invention fulfills this long-standing need and desire in the art.

SUMMARY OF THE INVENTION

The present invention describes multi-lumen catheter devices which are capable of delivering high concentrations of pharmaceutically active substances and varying types of electromagnetic energy to a selected site. As a result, the electromagnetic energy enhances the local tissue distribution of the active substance and improves the permeation of the substance into cells and tissues. These devices allow high concentrations to be delivered locally, however, when diluted by the body's fluid volume, the ultimate concentration delivered to distal tissue is extremely small. The high local concentration allows for greater efficacy in treatment, while the low distal concentration minimizes toxic or other unwanted effects in tissues that are not the target of the treatment.

The present invention relates to therapeutic treatments of blood vessels and other body passages and tissues that may be accessed through the body's passageways. The present invention further provides a device that delivers electromagnetic energy, along with a pharmaceutically active substance, to the site of therapy. By doing so, delivery of the active substance is enhanced. High local concentrations of a therapeutic substance is delivered to a target, which, if delivered systemically, would not be desirable due to systemic toxicity and other effects.

In one embodiment of the present invention, there is provided a catheter device for enhancing local delivery of a compound in a subject, said catheter comprising a first lumen for delivering electromagnetic energy to the subject; a second lumen for delivering the compound to the subject; a proximal end; and a distal end. Preferably, the proximal end comprises fiber optic attached to a source of electromagnetic energy; and a connection through which the compound is delivered into the second lumen. The distal end comprises a port through which the compound is delivered to the subject; and an optics assembly for transmitting the electromagnetic energy to the subject, wherein the optics assembly comprising an optic probe with a tip. Optionally, the catheter device further comprises a means to observe the placement of the tip, such as endoscope.

In another embodiment of the present invention, there is provided a catheter device for enhancing local delivery of a compound to a site of interest in a vascular vessel, comprising a first lumen for delivering electromagnetic energy to the site; a second lumen for delivering the compound to the site; and two inflatable chambers located on either side of the site, wherein a space is created between the two chambers. Preferably, the chambers are filled with Theological material. Optionally, the vascular vessel catheter device further comprising laser chips to be placed into the vascular vessel.

In still another embodiment of the present invention, there is provided a catheter device for enhancing local delivery of a compound to a body cavity, comprising a first lumen for delivering electromagnetic energy to the site; a second lumen for delivering the compound to the site; and single or multiple inflatable chambers filled with rheological material, wherein the chambers are placed in the cavity. An example of the body cavity is bladder.

In yet another embodiment of the present invention, there is provided a method for enhancing local delivery of a pharmaceutical compound to a subject, comprising the steps of irradiating the subject with electromagnetic energy and administering the pharmaceutical compound to the subject, wherein both the electromagnetic energy and the pharmaceutical compound is delivered through the catheter device disclosed herein.

In still yet another embodiment of the present invention, there is provided a method for increasing the diffusion rate of a substance in a medium, comprising the step of applying electromagnetic energy to the medium, wherein the electromagnetic energy generates propagating pressure wave upon the medium, and wherein the electromagnetic energy is delivered through the catheter device disclosed herein.

In still yet another embodiment of the present invention, there is provided a method for improving permeation rate of a molecule through a barrier, comprising the step of applying electromagnetic energy to the barrier, wherein the electromagnetic energy is delivered through the catheter device disclosed herein, and wherein the electromagnetic energy ablates or alters the structure of the barrier.

In still yet another embodiment of the present invention, there is provided a method for creating pores in a barrier thereby improving permeation rate of a molecule through the barrier, comprising the step of applying electromagnetic energy to the barrier, wherein the electromagnetic energy is delivered through the catheter device of disclosed herein.

The method disclosed herein may be used for treating a disease in a vascular vessel, a body cavity or other body passage.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
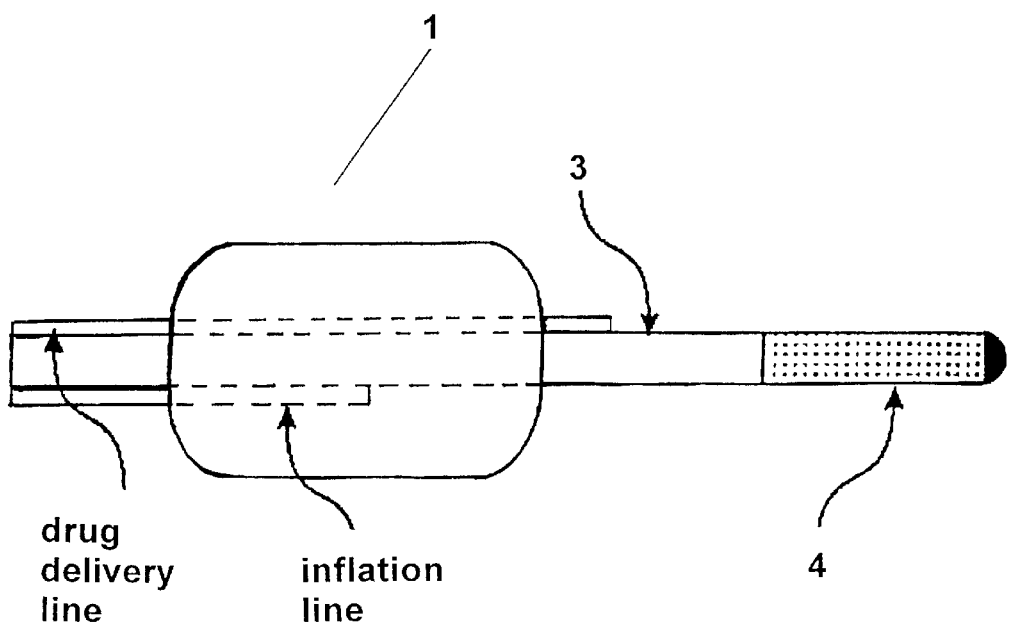
FIG. 1 shows a multi-lumen catheter 1 with a fiber optics assembly, which comprises fiber optic 3 and cylindrical scattering tip 4.

The present invention relates to therapeutic treatments of blood vessels and other body passages and tissues that may be accessed through the body's passageways. The present invention further provides a device that delivers electromagnetic energy, along with a pharmaceutically active substance, to the site of therapy. By doing so, delivery of the active substance is enhanced. High local concentrations of a therapeutic substance is delivered to a target, which, if delivered systemically, would not be desirable due to systemic toxicity and other effects.

Applied energy may act in several ways to drive agents into the treatment volume. In the present invention, non-ionizing electromagnetic energy (e.g. the infrared electromagnetic energy produced by an Er:YAG laser) is delivered by catheters and related devices to increase the diffusion rate of substances into or out of tissues. These methods, which are referred to as delivery of "optical pressure", "optical pumping", or "optical propulsion", involve the creation of a type of force which serves to increase the rate of diffusion of substances through tissue interfaces. In one aspect, propagating pressure waves are used to create pressure in a medium such that the diffusion rate of the substances in the medium, usually a drug formulation, is increased relative to its surrounding environment. In a related but distinctly different process, the momentum associated with propagating photons can also be applied directly to compounds in order to push these compounds through membranes or tissues. The latter process is referred to as "optical propulsion", which relies on the delivery of photons that are absorbed or scattered off molecules, thereby exchanging momentum with a net force in the direction of the light. Alternatively, a "trap," such as an optical trap, is formed to create the pressure effect, which essentially "pulls" the molecules along an electromagnetic field density gradient. Finally, electromagnetic energy used to alter molecular structures in the mucosa, or other tissue interface, is discussed as a means of "opening" pores to further improve permeation rates of molecules.

In one embodiment of the present invention, there is provided a catheter device for enhancing local delivery of a compound in a subject, comprising a first lumen for delivering electromagnetic energy to the subject; a second lumen for delivering the compound to the subject; a proximal end; and a distal end. Preferably, the proximal end comprises a fiber optic attached to a source of electromagnetic energy; and a connection through which the compound is delivered into the second lumen. The distal end comprises a port through which the compound is delivered to the subject; and an optics assembly for transmitting the electromagnetic energy to the subject, wherein the optics assembly comprising an optic probe with a tip. Optionally, the catheter device further comprises a means to observe the placement of the tip, such as endoscope, microscope and catheter. Representative examples of electromagnetic energy include laser, radiofrequency, light and microwave. The compound to be delivered can be a pharmaceutical compound including antibiotics, cytokines, anesthetic drugs, antineoplastic drugs, photodynamic therapeutical drugs, anti-infection drugs, anti-inflammatory drugs, clot-dissolving drugs.

In another embodiment of the present invention, there is provided a catheter device for enhancing local delivery of a compound to a site of interest in a vascular vessel, comprising a first lumen for delivering electromagnetic energy to the site; a second lumen for delivering the compound to the site; and two inflatable chambers located on either side of the site, wherein a space is created between the two chambers. Preferably, the chambers are filled with rheological material. Optionally, the vascular vessel catheter device further comprising laser chips to be placed into the vascular vessel.

In still another embodiment of the present invention, there is provided a catheter device for enhancing local delivery of a compound to a body cavity, comprising a first lumen for delivering electromagnetic energy to the site; a second lumen for delivering the compound to the site; and single or multiple inflatable chambers filled with rheological material, wherein the chambers are placed in the cavity. Examples of a body cavity include the bladder, intestine, airway, ureter and urethra.

In yet another embodiment of the present invention, there is provided a method for enhancing local delivery of a pharmaceutical compound to a subject, comprising the steps of irradiating the subject with electromagnetic energy and administering the pharmaceutical compound to the subject, wherein both the electromagnetic energy and the pharmaceutical compound is delivered through the catheter device disclosed herein. Preferably, the subject includes vascular vessels of a subject, lymphatic vessels of a subject, urethral vessels of a subject, colon passages of a subject, bladder of a subject, etc.

In still yet another embodiment of the present invention, there is provided a method for increasing diffusion rate of a substance in a medium, comprising the step of applying electromagnetic energy to the medium, wherein the electromagnetic energy generates propagating pressure wave upon the medium, and wherein the electromagnetic energy is delivered through the catheter device disclosed herein.

In still yet another embodiment of the present invention, there is provided a method for improving permeation rate of a molecule through a barrier, comprising the step of applying electromagnetic energy to the barrier, wherein the electromagnetic energy is delivered through the catheter device disclosed herein, and wherein the electromagnetic energy ablates or alters the structure of the barrier. Preferably, the barrier is a biological or non-biological barrier. Examples of biological barriers include skin, vaginal wall, uterine wall, intestinal wall, buccal wall, tongue, nasopharyngeal wall, anal wall, bladder wall, vascular vessel, lymphatic vessel and urethral vessel.

In still yet another embodiment of the present invention, there is provided a method for creating pores in a barrier thereby improving permeation rate of a molecule through the barrier, comprising the step of applying electromagnetic energy to the barrier, wherein the electromagnetic energy is delivered through the catheter device of disclosed herein.

The method disclosed herein may be used for treating a disease in a vascular vessel, a body cavity or other body passage.

Such method may also be used to treat a deep vein thrombosis in distal veins of the legs using Tissue Plasminogen Activator (TPA) or other clot dissolving drugs.

The following examples are given for the purpose of illustrating various embodiments of the invention and are not meant to limit the present invention in any fashion.

EXAMPLE 1
Pressure Wave Optical Pressure

Pressure waves created through the interaction of electromagnetic energy with tissue or non-biological matter may be used to drive molecules in a medium across tissue interfaces or between cellular junctions such as those found in membranes, between cells, or even through cellular membranes. For example, the interaction of laser irradiation with tissue can lead to the generation of propagating pressure waves (generated from a rapid volumetric change in the medium by heating, or by the generation of plasma) which are in the form of low pressure acoustic waves propagating at the speed of sound or high pressure shock waves propagating at supersonic speeds. These waves can also be a consequence of a generation of waves in a non-biological target that is in intimate acoustic contact with the biological media. These pressure waves may be applied to a pharmaceutical formulation in contact with the tissue to drive the substances in the formulation into the tissues. Continuously pulsing electromagnetic energy delivered in discrete short duration pulses propagates the pressure waves, which thereby creates a pressure that physically forces the substances in the formulation between cellular junctions or across membranes. The "pumping" effect may occur through the creation of increased pressure, including osmotic or atmospheric pressure. A separation results in a mobile phase due to the differential resistance of the tissues or membranes relative to the fluid medium.

To create low pressure waves propagating at the speed of sound, an example of efficacious irradiation parameters would be wavelength of 1064 nm, 20 ns pulses with energy of 20 mJ and a spot size of 1 mm. In the case of creating high pressure shock waves propagating at supersonic speeds, the same conditions would work except with a wavelength of 2.94 microns. Continuously pulsing electromagnetic energy delivered in discrete short duration pulses propagates the pressure waves that physically move substances across tissue interfaces and between cellular junctions. Solid state lasers can be easily configured to pulse at up to 40 Hz; alternatively, a diode-pumped micro-laser at 1064 nm and 1 ns pulses with a repetition rate of 10 kHz and peak power of 25 kW would be sufficient to produce low pressure waves.

EXAMPLE 2
Optical Propulsion

The aforementioned "pumping" effect may occur through the creation of increased pressure, including osmotic or atmospheric pressure. Continuous or pulsatile pressure may be applied directly to particles and molecules in a medium. In this aspect, the particulate or molecular object target would have different absorption or scatter characteristics than the medium such that the absorption or scatter of electromagnetic energy of the target results in an exchange of momentum from the photons to the target. As a result, the target is propelled at a differential rate relative to the medium. The ability of electromagnetic energy to push molecules through a medium is referred to as "optical propulsion." Optimally, the selected wavelength would neither result in a molecular nor electronic rearrangement as these two events would lead to the inefficient use of energy.

Light can exert forces on a molecule because photons carry momentum. The exchange of photon momentum with a molecule can occur incoherently, as in the absorption and readmission of photons, or coherently, as in the redistribution of (or lensing) of the incident field by the molecule.

Continuous or pulsatile pressure can be applied directly to particles and molecules in a medium using electromagnetic energy. For example, a drug could be conjugated to readily available colored polystyrene microspheres which absorb the electromagnetic energy from an diode-pumped Nd:YAG micro-laser (1064 nm, 1 ns pulses at a repetition rate of 10 kHz, peak power of 25 kW). Momentum is imparted unto the polystyrene sphere by the electromagnetic energy, and so is "pushed" in the direction of the propagation of the electromagnetic energy.

EXAMPLE 3
Incoherent Force

The incoherent interaction that can alter the momentum of an atom is also called the "scattering force" because it arises from direct scattering events. Every time an atom scatters a photon carrying momentum $p=h/\lambda$ (h is Planck's constant and $\lambda$ is the wavelength of light), the atom experiences a small change in velocity. In the case of incoherent scattering, two momentum impulses are delivered to the atom: one along the direction of the incident photon and the other opposite the direction of the scattered photon. Because the photons in rare media are not scattered into a preferred direction, the net average velocity change per scattered photon $\Delta v$ is opposite the direction of the incident photons with $\Delta v=p/M=h/\lambda M$, where M is the mass of the atom. Note that this force also provides a means to separate atomic or molecular species based on their mass, M.

The momentum imparted on the molecular target in an inelastic collision is equal to the ratio of the photon energy, U, divided by the speed of light, c. Given a critical amount of energy fluence (rate) in the electromagnetic energy continuous-wave beam or pulse, significant forces can be imparted on the molecular target, thereby inducing movement since force is equal to the time derivative of momentum.

This incoherent force could, for example, be used in the following way. The electromagnetic energy produced by a pulsed or continuous-wave Nd:YAG laser (1064 nm wavelength) could be used to irradiate a molecule (such as lidocaine-HCl) which does not significantly absorb energy having such wavelength. The molecule, if placed on the skin for example, would then scatter the electromagnetic energy in such a way that the net momentum imparted upon the molecule is in a direction away from the surface of the skin. Thus, the penetration of the drug into tissue would be enhanced as compared to passive diffusion.

EXAMPLE 4

Coherent Force

The force arising from a coherent interaction with light is also called the dipole force. The laser field polarizes the atom, and the polarized atom experiences a force in the gradient of an electromagnetic field. The strong electric field of a laser beam can be used to induce a dipole moment in a process called optical trapping. As long as the frequency of the laser field is below the natural resonances of the particle being trapped (e.g. below the atomic transition of an atom or the absorption band of a polystyrene sphere), the dipole moment is in phase with the driving electrical field. Because the energy, W, of the induced dipole, p, in the laser field, E, is given by $W=-pE$; the particle achieves a lower energy state by moving into the high-intensity focal spot of the laser beam. There have been numerous reports of optical traps being used to manipulate particles, or even cells. These traps are used to move these tiny particles around under a microscope objective. Optical tweezers have also been described whereby a focal spot of a single beam optical trap is moved with mirrors or lenses. It has also been shown that other forms of electromagnetic energy may be used to form such "traps."

In the present invention, a trap is formed at the tissue interface where a desired molecular target is to be moved in a particular direction. In the case of drug delivery, the desired direction is into the tissues. Thus, the focal point of the trap is moved along a vector that penetrates the tissue of interest, while a formulation containing the drug is applied to the surface of the tissue. In the case of an optical trap, the focal point of a single beam or multiple beam trap would then be moved progressively into the tissue, which could occur cyclically so as to ensure the maximum pumping effect. Besides optical traps, other types of traps, such as magnetic, radiofrequency or microwave traps would also be useful.

EXAMPLE 5

Applying Pressure to Permeabilized Membranes

A "pore" is created by first applying electromagnetic energy such that membrane or intramembrane structures are realigned, or the membrane is otherwise compromised, so as to improve permeation. This step may also be followed by application of a electromagnetic energy-induced pressure wave to drive molecules across tissue interfaces and between cellular junctions at a greater rate than can be achieved by either method alone. The energy may be delivered continuously or in discrete pulses to prevent closure of the drug pathway, or pore. Optionally, a different wavelength may be used in tandem to pump molecules through the pore than is used to create the pore. Alternatively, the energy source may be modulated so that pulse width and energy vary over time to alternately create a pore through which the subsequent pulse drives the molecule.

Transient pressure impulses have been described as a means of transiently permeabilizing membranes and tissue interfaces to certain compounds. Application of a continuous stream of such transient impulses makes continuous drug delivery possible. Further, dosage delivered may be regulated by modulating the energy, timing of pulses, or length of application.

In the present invention, laser energy is directed through optical fibers or guided through a series of optics. Pressure waves are generated in such a way that they come in contact with or create a gradient across the membrane surface or tissue interface. These pressure waves may be optionally used to create a pressure gradient to "pump" substances through the medium or across the membrane or tissue interface. This technology may be used for drug delivery across, for example, buccal, uterine, intestinal, urethral, vaginal, bladder and ocular membranes, as well as into obstructions that may exist in various passageways. Pharmaceutical compounds may be delivered into cellular spaces beyond the passageway walls, chambers encompassed by membranes or other tissue interfaces which may be accessed by these passageways.

EXAMPLE 6

Drug Formulations

Specific drug formulations were selected so that electromagnetic energy absorption or scatter is maximized relative to the surrounding medium. Many pharmaceutical or diagnostic compounds can be modified by the addition of energy absorbing or scattering groups to maximize optical propulsion of a particular formulation. A new class of compounds are defined that have unique permeability and migration characteristics in the presence of or following a treatment of electromagnetic energy. These molecules possess different characteristics by virtue of the addition of energy absorbing or scattering groups, which imparts momentum to the molecules and move the molecules relative to the surrounding medium.

Similarly, pharmaceutically active compounds may be modified by the addition of groups that readily form a dipole when exposed to appropriate electromagnetic energy, such as radiofrequencies or microwaves. The addition of such groups would result in enhanced ability to use optical trapping methods for the delivery of these types of compounds.

In general, any compound which may interact with electromagnetic energy in such a way that it is propelled through a medium may be used in the present invention. Thus, a means by which molecules may be propelled through a medium at differential rates relative to the medium and other molecules in the medium is defined. Also provided is a means by which molecules may be separated from one another based on their optical characteristics. The present invention is not limited to biomedical applications, as other separations of molecules may also be achieved by the methods described herein. Other examples include separating protein species in polyacrylamide gels, or separating oligonucleotides on microarray devices.

EXAMPLE 7
Catheter Device for the Urethra and Colon Passageways

The urethra and colon present passageways through which several organs may be treated as well as the passage walls themselves. In the case of bladder, prostate and colon cancer, access through these passageways by means of a catheter device presents an opportunity to directly treat membranes and tissues where cancerous cells reside. For example, a catheter device for treating colon, urethral or bladder walls may contain separate lumens for carrying a pharmaceutical substance, a fiber optic, and an endoscope. The proximal end of the catheter would have the fiber optic attached to a source of electromagnetic energy, preferably a laser capable of generating energies and wavelengths that result in membrane alterations, pressure waves or other means of increasing permeability or rate of diffusion of pharmaceutical substances. A separate lumen would be connected proximally to a syringe or other means of delivering said substance through the catheter to the site of action. The distal end of the device (the end which is inserted) would have a port through which substances are delivered, an optics assembly used to transmit the electromagnetic energy from the fiber optic to the tissue, and an endoscopic probe which allows the operator to visualize the location of the catheter tip assembly. Specifically, the catheter's laser optics assembly is placed against the site to be treated, a substance is released from another lumen, and electromagnetic energy is used to force the substance into the tissues.

Still in the same passageways, a similar catheter is used to treat prostate tissue. The catheter, when placed against the wall of the colon or bladder, can deliver a pharmaceutical substance and electromagnetic energy in such a way that the substance is forced across the colon or bladder wall into the surrounding tissue in high concentrations.

EXAMPLE 8
Catheter Device for Blood Vessels

Figure 4:
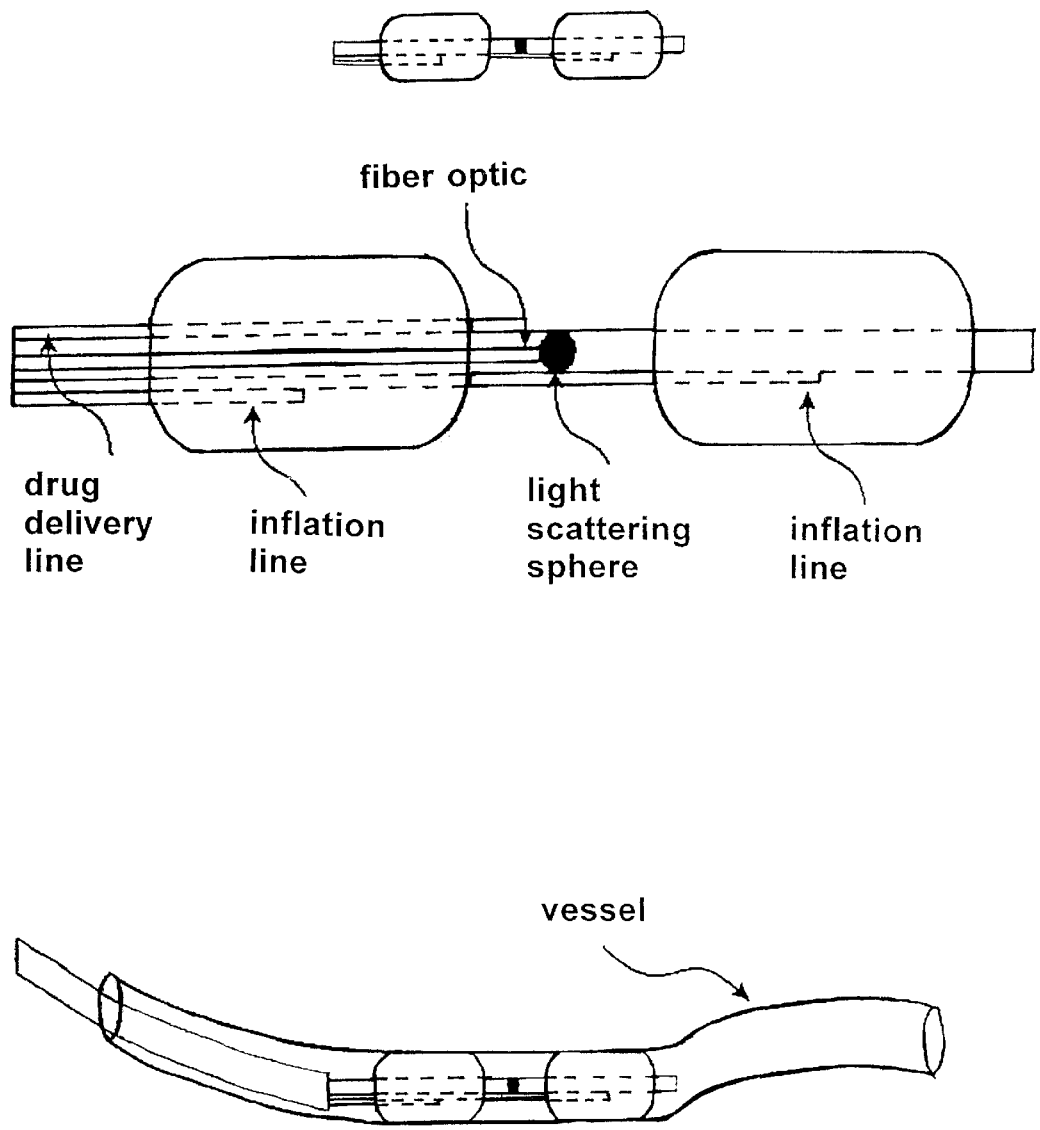
FIG. 4 shows a double balloon catheter with multiple lumens for blood vessels.

In a blood vessel, it is preferable to maintain blood flow so that nutrients and oxygen can reach the tissues downstream from a site to be treated. If blood flow is obstructed, ischemia may result and tissue damages beyond the site may be severe. In the case of coronary or carotid arteries, maintaining an adequate blood flow is critical to prevent adverse consequences such as infarction or stroke. Devices which accomplish this include catheter devices in which a space is created between two inflatable balloons (FIG. 4) located on either side of the site to be treated. Blood flow is obstructed to the site while allowed through a lumen in the catheter. An additional lumen may be used to deliver substances to the site of treatment. Thus, high concentrations of an active substance may be delivered locally with little or no effect on adjacent tissues. Concentrations of substances delivered locally may greatly exceed those achievable by intravenous routes.

Figure 2:
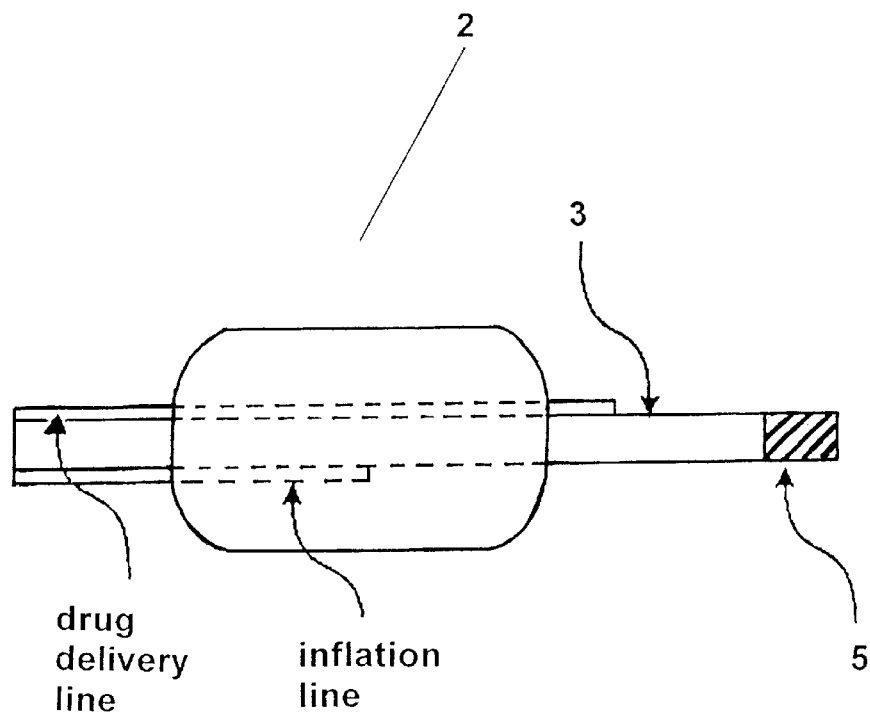
FIG. 2 shows a multi-lumen catheter 2 with a fiber optics assembly, which comprises fiber optic 3 and a passive Q-switched microchip laser 5.

An alternate catheter device for blood vessels utilizes microchip or diode lasers embedded in a single or multi-balloon cardiac catheter, whereby the catheter containing the laser chips is slid into position juxtaposed to a venous lesion such as a thrombus or plaque (FIGS. 1 and 2). Once the drug and electromagnetic energy have been delivered, the chambers are released allowing blood flow to pass the site of delivery, and the therapeutic substance is diluted by blood to sub-toxic levels.

Solid state Nd:YAG Q-switched microchip lasers are available from Uniphase Inc. These lasers are passively Q-switched and small enough that they can be optically bonded to the end of a silica optical fiber. The device can then be clad in a protective coating like epoxy or heat-shrink tubing. The microchip laser can be pumped by guiding the electromagnetic energy of a pulsed (up to 10 kHz) diode laser (available from SDL, Inc.). This microchip laser/optical fiber could then be passed through the catheter and placed within the body cavity of choice. The output of the laser can be passed through a cylindrical lens to allow formation of a roughly rectangular spot that could cover more, or all of the tympanic membrane. The 1064 nm electromagnetic energy output of the microchip laser would be efficacious at 100 microjoules/pulse.

Still alternatively, a fiber optic from an external source may be used in the catheter device for delivering electromagnetic energy to the site of therapy. CW or pulsed lasers with fiber optic leads may be used provided the optic terminus provides laser energy to the lesion or site to be treated.

EXAMPLE 9
Catheter Device Using Rheological Material-Filled Chambers

Figure 3A:
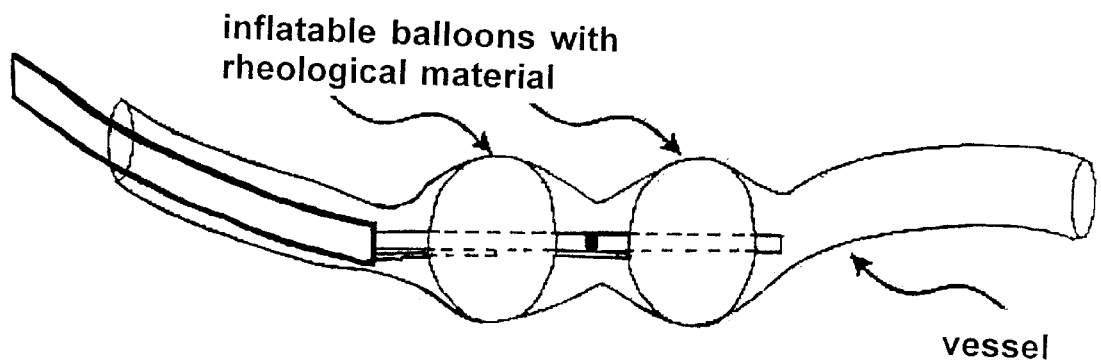
FIG. 3A shows a blood vessel catheter with inflatable balloons filled with rheological material.
Figure 3B:
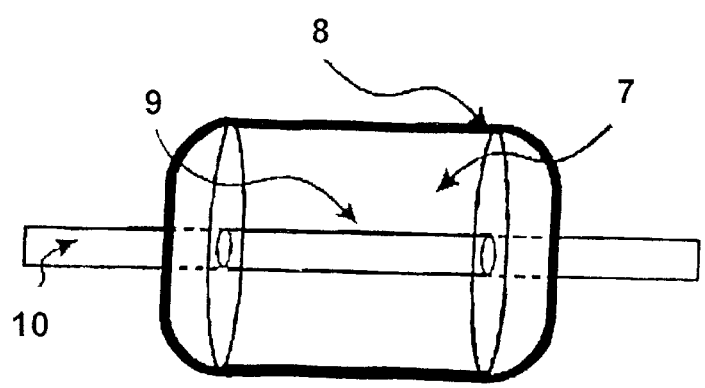
FIG. 3B shows a catheter 6 comprising a low compliance chamber 7 filled with rheological fluid, an outer electrode 8, an inner electrodes 9 and optical fiber 10.

Electrorheologic or magnetorheologic fluids are used to create obstruction in a vessel or other biological passageway (FIG. 3). Optionally, the balloons in the cardiac catheter are replaced with chambers containing electrorheologic or magnetorheologic fluids. Fluids become rigid when a magnetic field or electrical current is applied, thereby creating an obstruction in the vessel and allowing the space between them to be treated without affecting the regions upstream or downstream from the chambers. For example, cylindrical electrodes arranged colinearly around the central axis of the catheter could be charged with voltage (FIG. 3). This would serve to stiffen the Theological fluid (e.g. lithium polymethacrylate) encapsulated between the electrodes. The chamber may take the form of a high compliance chamber, which generally fills up the space in the vessel lumen to create an obstruction. Alternatively, the chamber may be a low compliance chamber that expands beyond the vessel walls, thereby stretching the walls. Such low compliance chamber would be useful for performing angioplasty, while high compliance chambers may be used for creating a blockage.

Electromagnetic energy delivered via a fiber optic device, or by microchip and diode lasers embedded in the catheter wall may then be used to effectively apply optical pressure such that substances co-delivered with the energy can be driven into the relevant tissues.

EXAMPLE 10
A Bladder Catheter Device with an Endoscope

Figure 5:
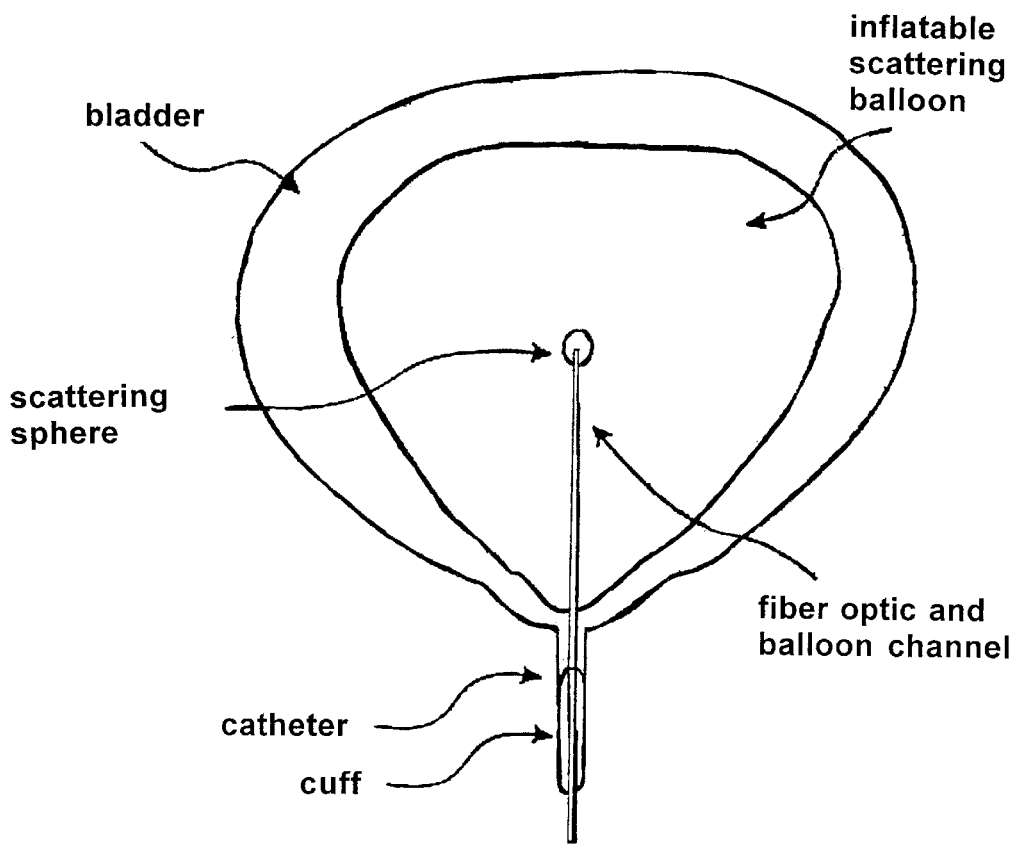
FIG. 5 shows a bladder catheter with an inflatable cuff and balloon for the treatment of large hollow cavities.

An imaging fiber optic can be passed down one of the channels of the catheter device, or a version of the catheter can itself be passed down the channel of a larger endoscope. In the case of the bladder catheter (FIG. 5), an endoscope (available from Olympus Inc.) has a hollow tube for drug delivery passed down one of the working channels. The tube is made from fine surgical tubing (available from Intramedics, Inc.). The proximal end of the tube is placed over a needle affixed on a syringe filled with the appropriate medicament. The distal end of the tube is placed in a cannula of approximately 14 gauge. Once a cuff is inflated in the ureter to contain fluids within the bladder, a solution of the appropriate medicament is injected into the bladder. A standard silicon optical fiber of 250 micron diameter (available from Edmund Scientific) is passed down another working channel of the endoscope and into the cannula adjacent to the drug tube. The distal end of the optical fiber terminates in a 1 mm diameter spherical diffusing tip (available from Miravant Inc.). The fiber tip is placed inside an inflatable balloon, which is attached to the catheter and filled with a scattering solution, such as Intralipid, once inside the bladder. The proximal end of the optical fiber is terminated in an SMA connector, which can be attached to a laser output coupling optical arrangement (available from Thor Labs Inc.). The electromagnetic energy coupled into the optical fiber is produced by a pulsed Nd:YAG laser (available from Spectra-Physics Lasers, Inc.). The pulse width is about 250 microseconds, the wavelength is 1064 nm, the pulse energy is about 10 mJ, the pulse repetition rate is about 20 Hz.

EXAMPLE 11
A Specific Design of Catheter Device for Blood Vessels

A catheter device for blood vessels is designed, which contains two chambers filled with a magnetorheologic fluid, a central lumen for blood flow, a separate lumen for delivering a therapeutic substance to the site between the chambers, and a third lumen containing fiber optics connected to a laser source. The catheter may be fed through the femoral or brachial artery until it reaches the coronary arteries. The chambers are located in such a way that one lies upstream and the other downstream from a blood clot or site of plaque formation. Blood flow through the catheter is enabled via a shunt from the artery to the central lumen. Optionally, once the catheter is in place, a therapeutic substance such as a clot-dissolving drug or a therapeutic agent is then supplied through an alternate lumen which has an opening between the two chambers. Once the substance floods the space between the chambers, electromagnetic energy supplied through a fiber optic may be used to actively pump the drugs into the vessel wall, or into the clot.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method for enhancing local delivery of a pharmaceutical compound to a site of interest in a body cavity within an individual, comprising the steps of:

providing access to the site of interest in said body cavity via a catheter device, said catheter device comprising:
  a first lumen for delivering electromagnetic energy, said electromagnetic energy selected from the group consisting of laser, radiofrequency, microwave, and light;
  a second lumen for delivering said pharmaceutical compound;
  a proximal end having fiber optics in said first lumen and a connection means for delivery of said pharmaceutical compound to said second lumen;
  a distal end having an optics assembly for transmitting said electromagnetic energy, said electromagnetic energy optionally transmitted via an optic probe comprising a tip, and a port for delivery of said pharmaceutical compound, wherein said first and second lumens are independently and operably connected between said proximal end and said distal end; and
  one or multiple chambers, said chamber comprising an electrode and a rheologic fluid;
placing said one or multiple chambers in said body cavity;
applying an electric current or a magnetic field to said rheologic fluid wherein said chamber(s) forms an obstruction in said body cavity;
delivering said pharmaceutical compound to the site of interest through the distal end of the second lumen of said catheter device; and
irradiating said site of interest with electromagnetic energy delivered through the distal end of the first lumen of said catheter device;
wherein said electromagnetic energy exerts an optical force comprising optical pressure, optical pumping or optical propulsion, said optical force acting on said pharmaceutical compound directly or indirectly to move said pharmaceutical compound to said site thereby enhancing local delivery of said pharmaceutical compound to said site of interest within an individual.

2. The method of claim 1, wherein the pharmaceutical compound is selected from the group consisting of antibiotics, cytokines, anesthetic drugs, antineoplastic drugs, photodynamic therapeutical drugs, anti-infection drugs, anti-inflammatory drugs, and clot-dissolving drugs.

3. The method of claim 1, wherein said body cavity is selected from the group consisting of bladder, intestine, airway, ureter, and urethra.

4. The method of claim 1, wherein said method effects treatment of a disease at the site of interest in said body cavity.

* * * * *